(12) United States Patent
Backman et al.

(10) Patent No.: US 7,540,857 B2
(45) Date of Patent: Jun. 2, 2009

(54) SELF SUTURING ANCHOR DEVICE

(75) Inventors: D. Kent Backman, Salt Lake City, UT (US); Brian Stevens, Pleasant Grove, UT (US); Greg McArthur, Sandy, UT (US); William Padilla, Sandy, UT (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 606 days.

(21) Appl. No.: 11/202,484

(22) Filed: Aug. 11, 2005

(65) Prior Publication Data

US 2008/0015509 A1 Jan. 17, 2008

Related U.S. Application Data

(63) Continuation-in-part of application No. 11/198,666, filed on Aug. 5, 2005, now Pat. No. 7,470,256, which is a continuation-in-part of application No. 11/082,170, filed on Mar. 16, 2005.

(60) Provisional application No. 60/623,502, filed on Oct. 29, 2004, provisional application No. 60/627,485, filed on Nov. 12, 2004.

(51) Int. Cl.
*A61M 5/32* (2006.01)

(52) U.S. Cl. ..................................... 604/180

(58) Field of Classification Search ......... 604/116–117, 604/174–180; 606/139–153
See application file for complete search history.

(56) References Cited

U.S. PATENT DOCUMENTS

| | | | | |
|---|---|---|---|---|
| 2,669,231 A | * | 2/1954 | Fisher | 604/179 |
| 4,372,073 A | * | 2/1983 | Goldman | 43/57.1 |
| 4,869,719 A | | 9/1989 | Hogan | 604/174 |
| 4,874,380 A | | 10/1989 | Hesketh | 604/180 |
| 5,224,935 A | | 7/1993 | Hollands | |
| 5,416,952 A | | 5/1995 | Dodge | |
| 5,911,229 A | | 6/1999 | Chodorow | |
| 6,138,866 A | | 10/2000 | Lambelet, Jr. et al. | |
| 6,554,297 B2 | | 4/2003 | Phillips et al. | |
| 2001/0037119 A1 | | 11/2001 | Schmieding | |
| 2002/0072713 A1 | | 6/2002 | Almond et al. | |
| 2006/0095008 A1 | | 5/2006 | Lampropoulos et al. | |
| 2006/0095009 A1 | | 5/2006 | Lampropoulos et al. | |

OTHER PUBLICATIONS

European Search Report, PCT/US2005/038910 dated Aug. 20, 2007, 8 pages.

(Continued)

*Primary Examiner*—Nicholas D Lucchesi
*Assistant Examiner*—Nathan R Price
(74) *Attorney, Agent, or Firm*—Ryan D. Benson; Stoel Rives, LLP

(57) ABSTRACT

A catheter securement device which automatically deploys one or more sutures to secure a catheter without requiring the practitioner to manually suture the catheter to the self-suturing anchor device. A ratchet mechanism having one or more rotatable ratchet members which pivot and a ratchet member engagement spring which maintains contact between the teeth of the rotatable ratchet member and the teeth of the ratchet ring. An O-ring is provided to maintain the position of the sutures to minimize disruption of the sutures before deployment of the sutures. In one embodiment, a stationary base of the anchor device comprises a single molded member. In another embodiment a method of manufacturing the catheter anchor device comprising welding a rotatable ring and one or more bearing members of the catheter anchor device through access bores in the stationary base.

9 Claims, 10 Drawing Sheets

OTHER PUBLICATIONS

International Search Report and Written Opinion—Apr. 10, 2008.
International Search Report and Written Opinion—Jun. 14, 2006.
US Office Action for U.S. Appl. No. 11/535,454, filed Jul. 28, 2008.
US Office Action for U.S. Appl. No. 11/532,056, filed Jul. 29, 2008.

* cited by examiner

SELF SUTURING ANCHOR DEVICE

CROSS-REFERENCE TO RELATED APPLICATIONS

This application is a continuation-in-part application of U.S. Nonprovisional Patent Application Ser. No. 11/198,666, filed on Aug. 5, 2005 now U.S. Pat. No. 7,470,256, entitled "Self-suturing Anchor Device for a Catheter," which claims the benefit of priority as a continuation-in-part to U.S. Nonprovisional Patent Application Ser. No. 11/082,170, filed on Mar. 16, 2005, entitled "Self-suturing Anchor Device for a Catheter," which claims the benefit of priority to U.S. Provisional Patent Application Ser. No. 60/627,485, filed on Nov. 12, 2004, entitled "Self Suturing Anchor Device for a Catheter" and to U.S. Provisional Patent Application Ser. No. 60/623,502, filed on Oct. 29, 2004, entitled "Self Suturing Anchor Device for a Catheter, " for which the entire specifications of all of the aforementioned applications are incorporated herein by reference.

BACKGROUND OF THE INVENTION

1. The Field of the Invention

Exemplary embodiments of the present invention relate to the field of catheters, and, more particularly, to a self-suturing anchor device for use with a catheter.

2. Background and Relevant Art

Catheters play an important role in the treatment and care of patients in modern medicine. In particular, catheters provide relatively unobtrusive access to remote portions of a patient's body, allowing desired procedures or treatments to be performed. A wide variety of generalized and specialized catheters have been developed and refined for particular uses. For example, angioplasty catheters have been adapted to provide a safe and effective conduit for the delivery of a stent and/or balloon to a narrowing or loading blockage in a patient's artery or vein. Drainage catheters are configured to be inserted into a cavity surrounding a patient's kidney, liver or other organ to drain excess fluid or infection from the cavity.

In addition, a number of devices and implements have been developed for use with catheters, to facilitate their effectiveness, or to overcome inherent difficulties associated with their use. For example, catheters that are designed to remain placed in a patient for long periods of time, such as for ongoing care or treatment of the patient, present a number of difficulties. Such catheters must be secured to the patient in a manner that minimizes movement of the catheter that could harm the patient, or otherwise interrupt proper functioning of the catheter.

Accordingly, one approach in the prior art has been to suture the catheter directly to the patient's skin. However, when a patient repositions himself/herself in bed, the catheter may pull at the suture site or bend the catheter. Another approach is to inflate a balloon associated with the distal end of the catheter inside the patient. However, at times an incoherent patient may attempt to withdraw or otherwise remove the catheter. This can cause injury to the catheter insertion site, or can interfere with proper operation of the catheter.

In view of these and other problems in the art, a number of devices have been developed to secure a catheter in a manner that minimizes movement of the catheter, or minimizes interference with its proper operation. Typically, such devices include an adhesive layer to be secured to the patient with a small bore for accommodating the catheter and an adhesive strip to secure the catheter relative to the adhesive layer. Devices such as these are useful because they can be employed by a practitioner to secure the desired positioning of the catheter. Such devices, however, can be undesirable due at least in part to the fact that they typically cover or otherwise obstruct the catheter insertion site. This can make it difficult to identify infections, drainage, or other complications that may occur at the catheter insertion site. Furthermore, the devices can also obstruct cleaning of the insertion site, such that the site can only be cleaned by removing the anchor devices. Additionally, conventional anchor devices typically utilize a clip, or other securement member which typically is rigid or has a high profile when utilized to secure the catheter. As a result, the securement device can be uncomfortable if pressed against the patient by a chair, bed, or other object.

BRIEF SUMMARY OF THE INVENTION

The present invention is directed to a catheter securement device which automatically secures the catheter without requiring the practitioner to manually suture the catheter to the self-suturing anchor device. The self-suturing anchor device has a securement mechanism which is adapted to be actuated by the user to automatically secure the catheter in a quick and efficient manner.

In one embodiment, a rotatable ring is provided in connection with the self-suturing anchor device to automatically secure the catheter. A pair of suture threads extend from the bottom of the rotatable ring. When a user pulls the threads in a rearward direction, the threads automatically secure a portion of the catheter associated with the bottom of the rotatable ring. The user can then rotate the rotatable ring in one or both of a clock-wise or a counter clock-wise direction. Rotation of the rotatable ring automatically secures the portion of the catheter positioned centrally within the rotatable ring.

The rotatable ring is utilized in connection with a ratchet mechanism. The ratchet mechanism allows movement of the rotatable ring in a first direction while preventing movement of the rotatable ring in the opposite direction. As a result, the rotational position of the rotatable ring is secured against movement in a rearward direction. When the user rotates the rotatable ring to deploy, secure, and/or tighten the sutures relative to the catheter, inadvertent movement of the rotatable ring does not result in loosening of the sutures. Additionally, where the tension on the sutures decreases due to factors such as the natural loosening of the fibers of the suture, the user can easily ratchet the rotatable ring an additional amount to return the sutures to a desired degree of tensioning.

The ratchet mechanism includes rotatable ratchet members. The rotatable ratchet members pivot allowing for movement of the portion of the rotatable ratchet member having teeth. Additionally, a ratchet member engagement spring is provided which maintains contact between the teeth of the rotatable ratchet member and teeth of the ratchet ring. The ratchet member engagement spring can flex or undergo other deformation to allow for sliding of the teeth of the rotatable ratchet member over the teeth of the ratchet ring during rotation of the rotatable ring.

In one embodiment, an O-ring is provided to maintain the position of the sutures beneath the rotatable ring. The O-ring is configured to be positioned between the rotatable outer ring and base. Maintaining the position of the sutures minimizes disruption of the sutures before deployment of the sutures. In another embodiment, the base of the anchor device comprises a single molded member. The single molded member is formed utilizing first and second mold members. The base includes an undercut. As a result, the first mold member and the second mold member are formed to provide the undercut during the molding of-the base.

According to one embodiment of the present invention, a method of assembling the catheter anchor device is provided. Loading of the sutures is facilitated by mounting the base of the anchor device on a loading block. A suture loading cylinder is positioned through the center bore of the catheter anchor device and the center aperture. The suture loading cylinder is utilized to provide a quick and effective mechanism for forming the loop configurations of the first suture, the second suture, and the third suture and for loading the sutures in the base. According to another embodiment of the present invention, one or more components of the catheter anchor device are welded to facilitate assembly of the catheter anchor device. For example, a plurality of pins of the rotatable outer ring are configured to be welded to securement bores of the bearing members. A plurality of access bores are provided in connection with the base of the anchor device such that a welding tool can be inserted through the access bores of the catheter anchor device to weld the pins of the rotatable outer ring to the securement bores of the bearing member.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
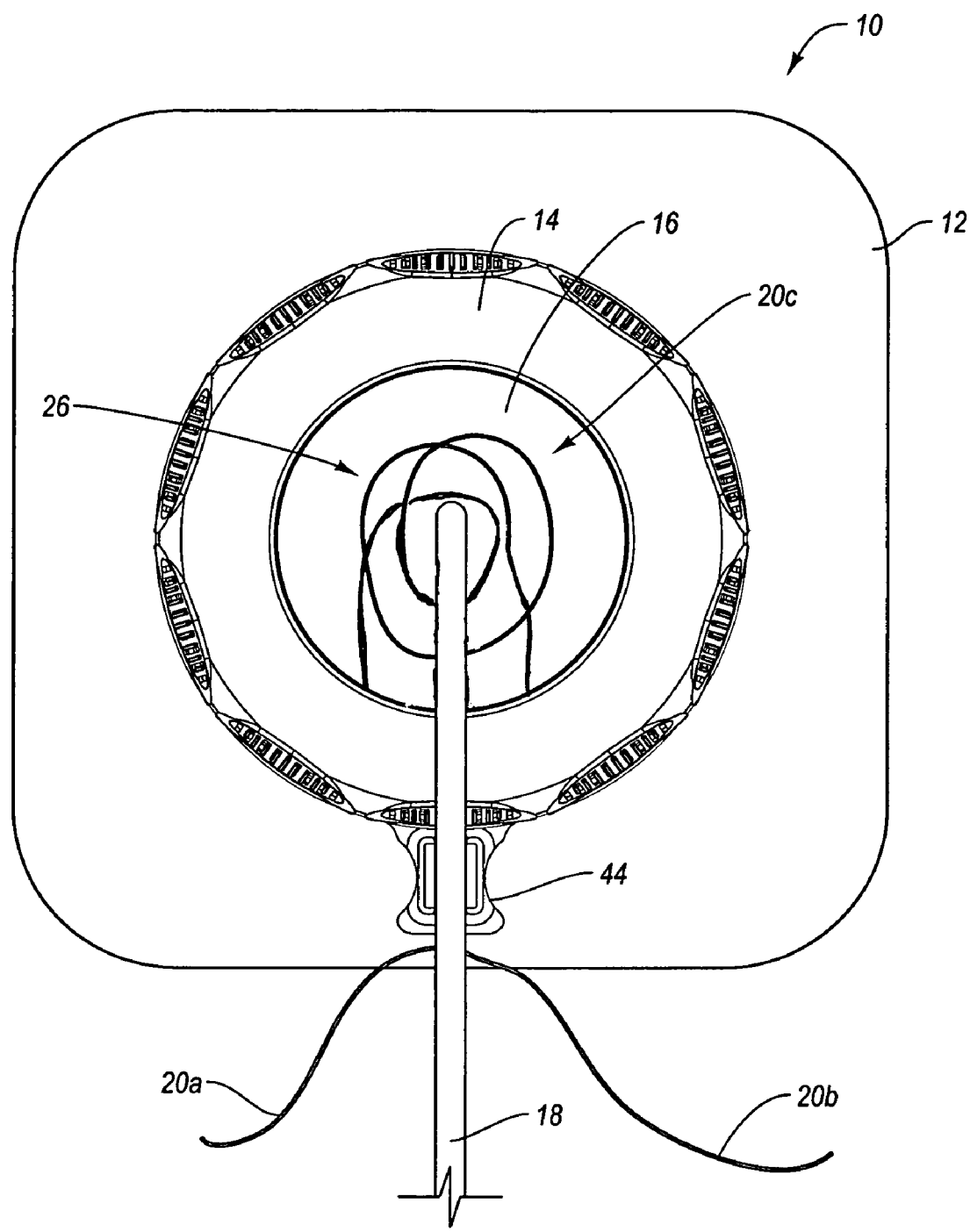
FIG. 1 is a front perspective view of the catheter anchor device illustrating deployment of a first suture.

The present invention is directed to a catheter securement device which automatically secures the catheter without requiring the practitioner to manually suture the catheter to the self-suturing anchor device. The self-suturing anchor device has a securement mechanism which is adapted to be actuated by the user to automatically secure the catheter in a quick and efficient manner.

The rotatable ring is utilized in connection with a ratchet mechanism. The ratchet mechanism allows movement of the rotatable ring in a first direction while controlling movement of the rotatable ring in the opposite direction. As a result, the rotational position of the rotatable ring is secured against movement in a rearward direction. The ratchet mechanism includes rotatable ratchet members. The rotatable ratchet members pivot allowing for slight movement of the portion of the rotatable ratchet member having the teeth. Additionally, a ratchet member engagement spring is provided which maintains contact between the teeth of the rotatable ratchet member and the teeth of the ratchet ring. The ratchet member engagement spring can flex or undergo other deformation to allow for sliding of the teeth of the rotatable ratchet member over the teeth of the ratchet ring during rotation of the rotatable ring.

In one embodiment, an O-ring is provided to maintain the position of the sutures beneath the rotatable ring. The O-ring is configured to be sandwiched between the rotatable outer ring and the base. Maintaining the position of the sutures minimizes disruption of the sutures before deployment of the sutures. In another embodiment, the base of the anchor device comprises a single molded member. The single molded member is formed utilizing first and second mold members. The base includes an undercut. As a result, the first mold member and the second mold member are formed to provide the undercut during the molding of the base.

According to one embodiment of the present invention, a method of assembling the catheter anchor device is provided. Loading of the sutures is facilitated by mounting the base of the anchor device on a loading block. A suture loading cylinder is positioned through the center bore of the catheter anchor device and the center aperture. The suture loading cylinder is utilized to provide a quick and effective mechanism for forming the loop configurations of the first suture, the second suture, and the third suture and for loading the sutures in the base. According to another embodiment of the present invention, one or more components of the catheter anchor device are welded to facilitate assembly of the catheter anchor device. For example, a plurality of pins of the rotatable outer ring are configured to be welded to securement bores of the bearing members. A plurality of access bores are provided in connection with the base of the anchor device such that a welding tool can be inserted through the access bores of the catheter anchor device to weld the pins of the rotatable outer ring to the securement bores of the bearing member.

FIG. 1 is a perspective view of anchor device 10 according to one embodiment of the present invention. Anchor device 10 is utilized to secure a catheter relative to a patient while allowing access to a catheter insertion site for observation and care of the catheter insertion site. Anchor device 10 provides a simple and effective mechanism for securing a catheter by automatically deploying one or more sutures to secure the catheter. In the illustrated embodiment, anchor device 10 comprises an adhesive sheet 12, rotatable ring 14, and a center aperture 16. A catheter 18 is shown being utilized in connection with anchor device 10. Catheter 18 has been inserted into the patient at a catheter insertion site 26.

Anchor device 10 has been placed over catheter 18 such that catheter 18 is threaded through the middle of center aperture 16. Catheter insertion site 26 is positioned approximately in the middle of center aperture 16 such that rotatable ring 14 is positioned and centered about catheter insertion site 26. Adhesive sheet 12 has an adhesive backing which securely fastens anchor device 10 to the patient before and after deploying of the sutures of anchor device 10. Rotatable ring 14 is utilized to automatically deploy one or a plurality of sutures for securement of catheter 18.

Center aperture 16 is configured to allow access to catheter 18 at the catheter insertion site 26. By providing access to catheter insertion site 26, a practitioner can observe the condition of the catheter insertion site 26 and provide treatment and care of the catheter insertion site 26 as needed. This can be important in the event of injury, infection, drainage, or other disruptions of catheter insertion site 26. The ability to care for catheter insertion site 26 can be quiet helpful, particularly where catheter 18 is utilized in a gastric or similar setting where regular care and treatment of the catheter insertion site is necessary to maintain the health of the patient and proper operation of catheter 18.

In the illustrated embodiment, a first suture 20, which is utilized to secure catheter 18, is shown being deployed. First suture 20 comprises a first end 20a, a second end 20b, and a loop portion 20c. A user grasps first end 20a and second end 20b. The user then retracts first end 20a and second end 20b in a rearward fashion to deploy the loops of the loop portion 20c of first suture 20. In the illustrated embodiment, the loop portion 20c of first suture 20 is a double loop forming a clove hitch-type securement knot. As the user continues to retract first end 20a and second end 20b, loop portion 20c continues to tighten about catheter 18 at a position adjacent rotatable ring 14. The configuration of first suture 20 provides a simple, quick, and effective mechanism for securing a portion of catheter 18 relative to rotatable ring 14. In a matter of seconds, first suture 20 can be actuated and fully deployed to secure catheter 18 relative to rotatable ring 14 and other portions of anchor device 10. When loop portion 20c is fully deployed and securely fastened about catheter 18, first end 20a and second end 20b can then be tied about the portion of catheter 18 corresponding with extension saddle 44. This provides two different points of securement of catheter 18 relative to anchor device 10. By providing two points of securement, first suture 20 minimizes twisting and/or pulling of catheter 18 that could result in injury of the patient tissue at catheter insertion site 26.

As will be appreciated by those skilled in the art, a variety of types and configurations of anchor devices can be utilized without departing from the scope and spirit of the present invention. For example, in one embodiment, only a first suture is utilized to secure the catheter. In another embodiment, string is used in the place of conventional suture material. In yet another embodiment, the suture is comprised of a monofilament material, woven silk thread, or other known or conventional string, wire, and/or suture materials.

Figure 2:
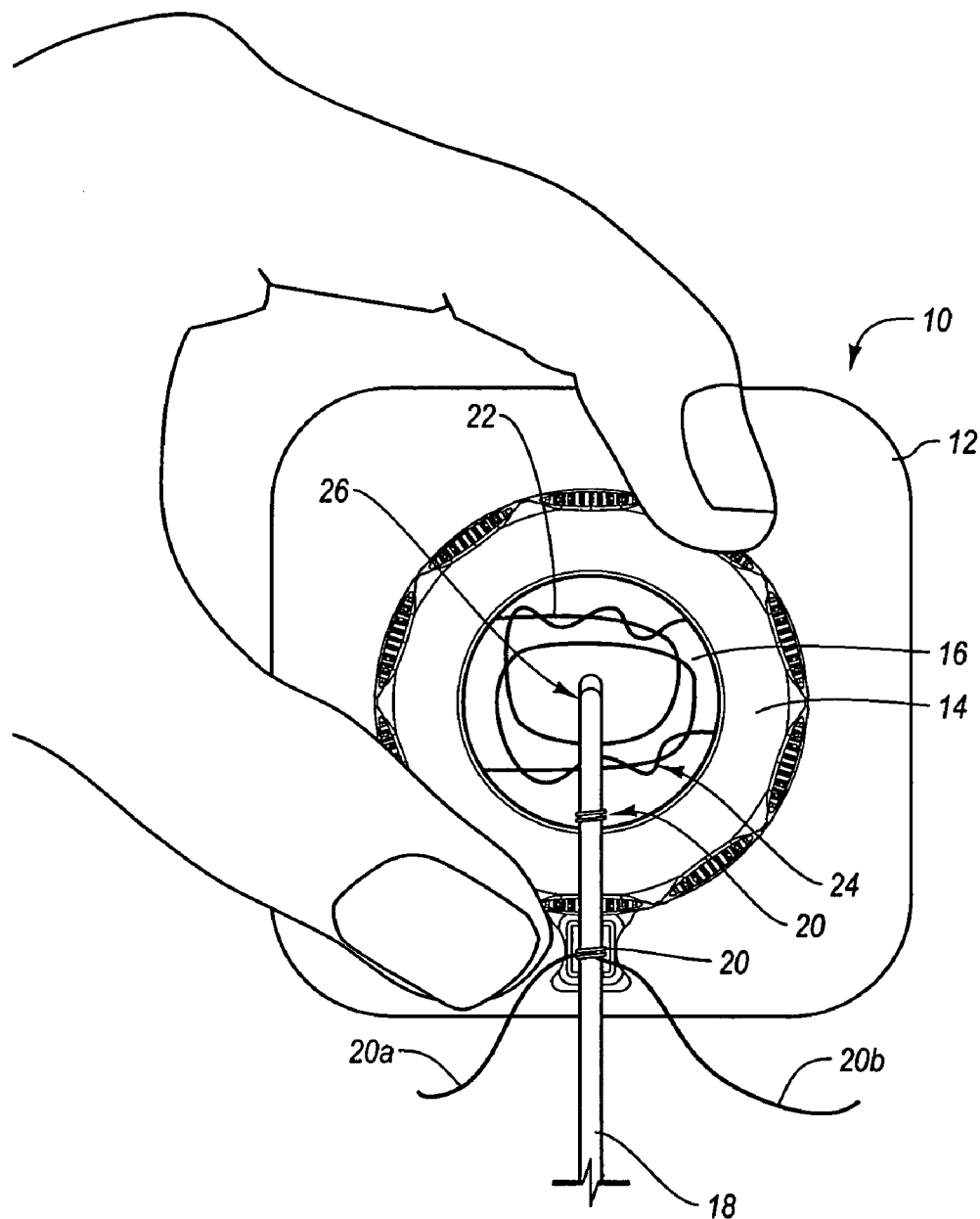
FIG. 2 is a front perspective view of the catheter anchor device illustrating deployment of a second suture and third suture relative to the catheter.

FIG. 2 is a top view of anchor device 10 illustrating a user actuating rotatable ring 14 of anchor device 10, according to one embodiment of the present invention. In the illustrated embodiment, first suture 20 has been fully deployed with the loop portion securely fastened about catheter 18 adjacent rotatable ring 14, and the first and second ends 20a and 20b have been tied to secure catheter 18 adjacent extension saddle 44.

In the illustrated embodiment, anchor device 10 includes a second suture 22 and third suture 24, which are housed beneath rotatable ring 14 prior to actuation of rotatable ring 14. Once first suture 20 is deployed, a user begins to rotate rotatable ring 14 to deploy second suture 22 and third suture 24. As the user rotates rotatable ring 14, second suture 22 and third suture 24 automatically deploy from beneath rotatable ring 14 and begin to loop about the portion of catheter 18 adjacent catheter insertion site 26. In the illustrated embodiment, the ends of second suture 22 and third suture 24 are actuated from opposite sides of rotatable ring 14 such that both second suture 22 and third suture 24 anchor catheter 18 from opposite sides of the catheter insertion site 26. As a result, two lateral securement positions are provided on each side of catheter 18 to minimize unintentional movement of catheter 18 at catheter insertion site 26. Securement of catheter 18 at catheter insertion site 26 will be discussed in more detail with respect to FIG. 3. The loops of second suture 22 and third suture 24 are formed using a double or triple knot configuration to provide a slip resistant knot when secured to catheter 18. The ability of the loop portion to secure catheter 18 will be discussed in more detail with respect to FIG. 3.

As will be appreciated by those skilled in the art, a variety of types and configurations of anchor device 10 can be utilized without departing from the scope and spirit of the present invention. For example, a single suture can be provided in connection with deployment of the rotatable ring rather than two sutures. In another embodiment, more than two sutures are provided in connection with deployment of rotatable ring 14. In yet another embodiment, a plurality of rotatable rings are provided with each rotatable ring deploying one or more sutures to secure catheter 18 in subsequent steps of actuation during use of the anchor device.

Figure 3:
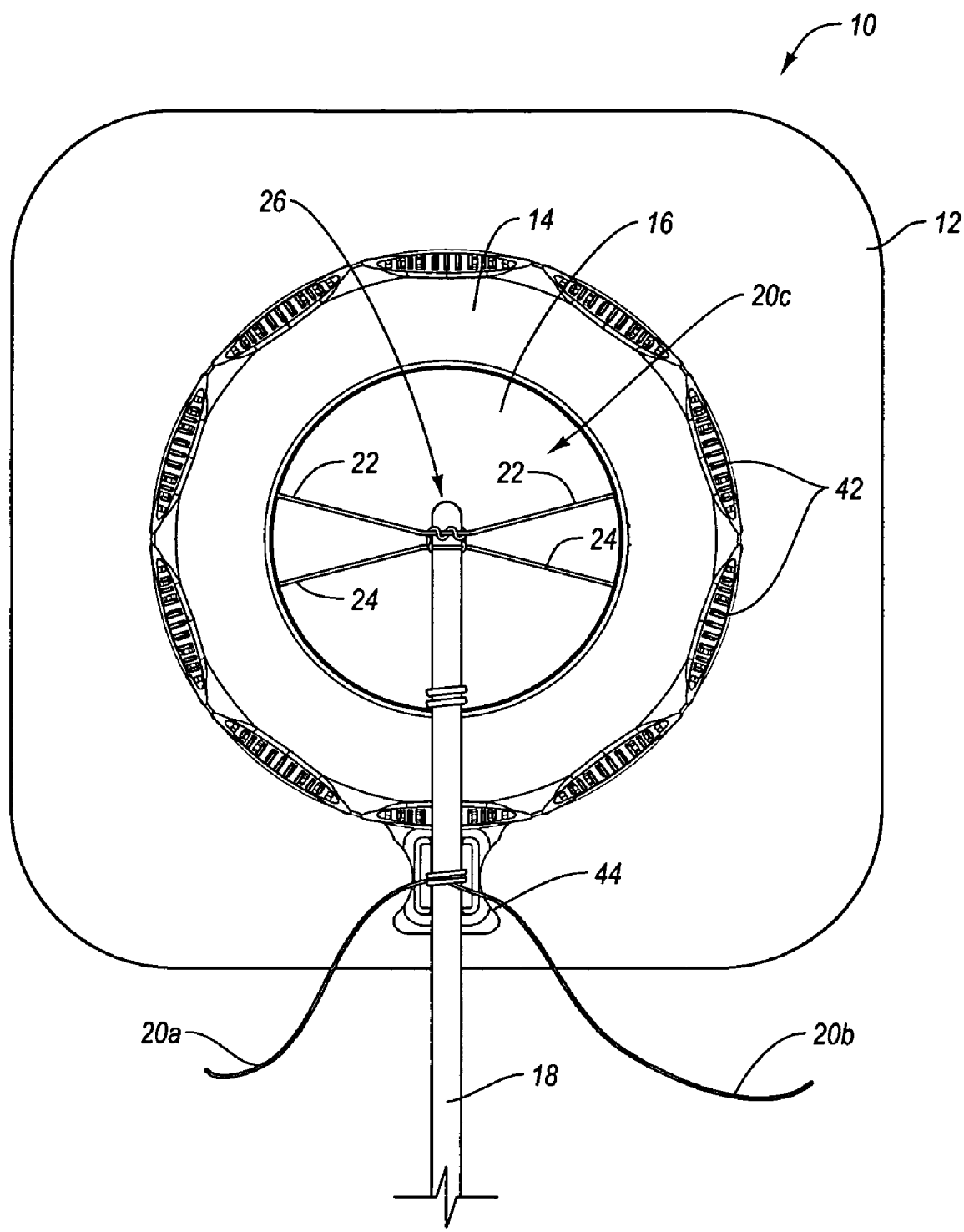
FIG. 3 is a front perspective view of a catheter anchor device illustrating securement of the catheter subsequent to deployment of the sutures.

FIG. 3 is a top perspective view of anchor device 10 subsequent to deployment of rotatable ring 14. In the illustrated embodiment, catheter 18 is secured by first suture 20, second suture 22, and third suture 24, subsequent to deployment of rotatable ring 14 and first suture 20. First suture 20 secures catheter 18 adjacent the bottom of rotatable ring 14 and at extension saddle 44. Extension saddle 44 provides a desired degree of displacement between the points of securement provided by suture 20 relative to catheter 18. The displacement provided between the points of securement of first suture 20 is sufficient to substantially minimize kinking, twisting, or other manipulation of catheter 18 that could result in damage to the patient tissue at catheter insertion site 26 resulting from movement of catheter 18. Additionally, extension saddle 44 provides a groove which accommodates catheter 18 to minimize kinking, pinching, or other pressure on catheter 18 from the transition over the top of rotatable ring 14.

The portion of catheter 18 positioned adjacent catheter insertion site 26 is secured by second suture 22 and third suture 24. One portion of second suture 22 is positioned on the left side of rotatable ring 14, while a second portion of second suture is secured adjacent the right side of rotatable ring 14. One portion of third suture 24 is secured adjacent the left side of rotatable ring 14, while the second portion of second suture 22 is secured adjacent the right side of rotatable ring 14. Additionally, the first portions of second suture 22 and third suture 24 on the left side of rotatable ring 14 are positioned at a displacement between five and 65 degrees or more relative to one another to provide securement of catheter 18 to minimize forward and rearward movement of catheter 18 during use of the anchor device 10. Additionally, the second portions of second suture 22 and third suture 24 on the right side of rotatable ring 14 are positioned at an angle of between five and 65 degrees or more relative to one another to minimize forward and rearward movement of the catheter 18 which could result in injury at catheter insertion site 26. As a result, a total of four separate points of securement are provided at the portion of catheter 18 adjacent catheter insertion site 26 to minimize both lateral and forward and rearward movement of catheter 18 during usage of catheter anchor device 10. This provides a safe and reliable securement of catheter 18 during usage while also providing access to the catheter insertion site for cleaning and care of the catheter and/or patient tissue at the catheter insertion site 26. In the illustrated embodiment, a plurality of scallops 42 are shown on rotatable ring 14. Scallops 42 facilitate gripping of rotatable ring during actuation of rotatable ring as shown in FIG. 2. Scallops 42 comprise a concave depression in the outward surface of rotatable ring 14. By providing a concave depression in the outward surface of rotatable ring 14, scallops 42 provide gripping members which minimize any potential abrasion to the patient or practitioner utilizing anchor device 10.

The configuration of anchor device 10 and rotatable ring 14 allow for quick, simple, and effective securement of catheter 18 subsequent to placement of catheter 18 in a patient. This not only shortens the length of the catheter securement procedure and thus the entire catheter placement procedure, but also is sufficiently simple such that an assisting nurse or other caretaker can secure catheter 18 while the physician attends to other aspects of the procedure being performed. This is not only more efficient from the standpoint of operating room economics, but can also be quite helpful in time sensitive procedures such as in a trauma setting or emergency situation.

Figure 4:
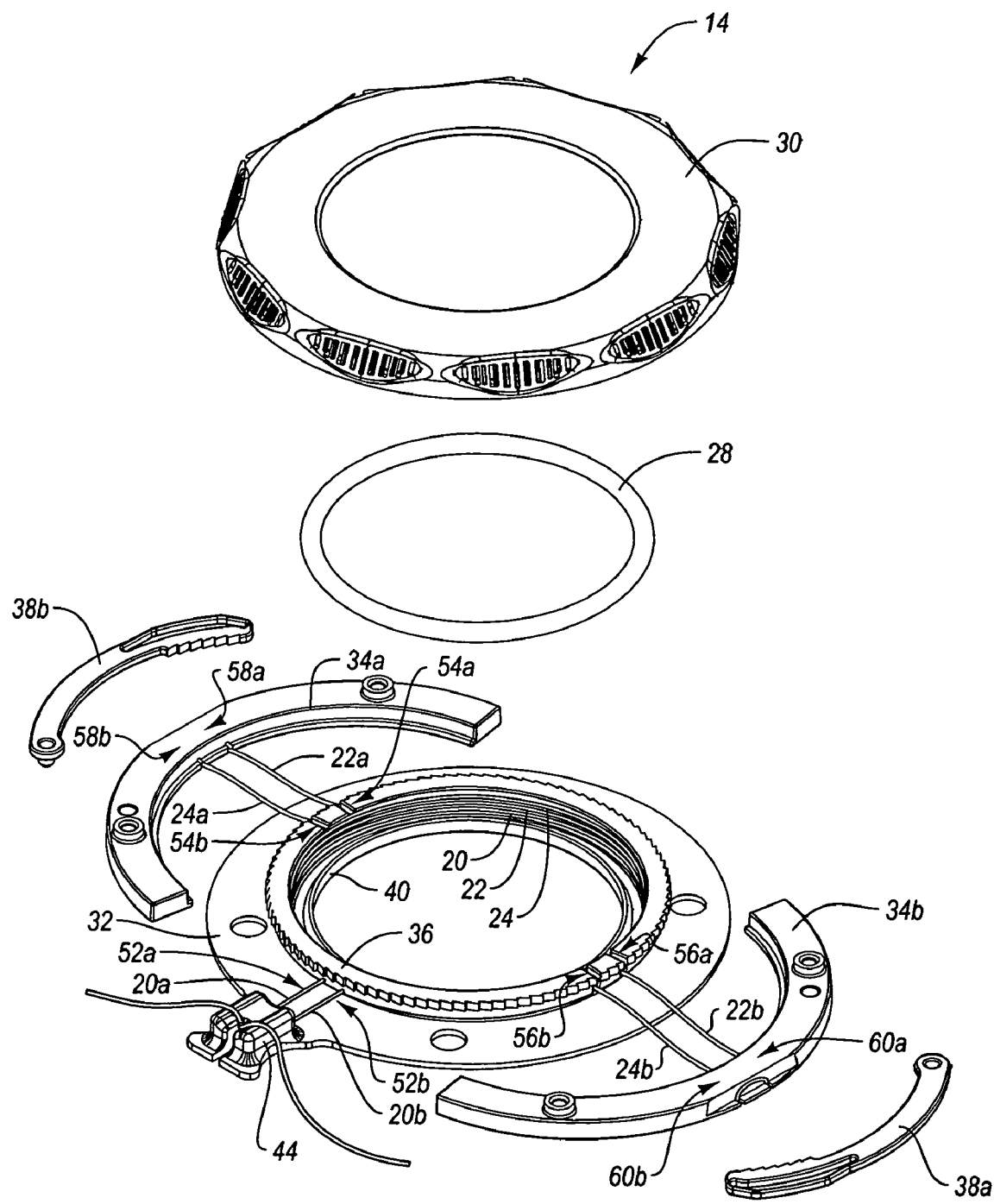
FIG. 4 is an exploded view of the catheter anchor device illustrating the components of the catheter anchor device including an O-ring and rotatable ratchet members.

FIG. 4 is an exploded view of rotatable ring 14 of anchor device 10 depicting a ratchet mechanism. In the illustrated embodiment, rotatable outer ring 30 and bearing members 34a, b are shown separated from base 32. A plurality of pin members are positioned beneath rotatable outer rings. The pin members are configured to be positioned in bearing members 34a, b to secure bearing members 34a, b to rotatable outer ring 30.

Bearing members 34a, b are configured to be positioned between rotatable outer ring 30 and base 32. Bearing members 34a, b contact base 32 beneath ratchet ring 36 such that bearing members 34a, b do no contact the teeth of ratchet ring 36. Similarly, bearing members 34a, b contact rotatable outer ring 30 beneath rotatable ratchet members 38a, b such that bearing members 34a, b do not contact the teeth of rotatable ratchet members 38a, b. As a result, bearing members 34a, b do not interfere with the cooperative engagement between ratchet members 38a, b and ratchet ring 36.

A lip on each of bearing members 34a, b extend inwardly beneath ratchet ring 36. When rotatable outer ring 30 is secured to bearing members 34a, b, the lateral positioning of bearing members 34a, b secures both bearing members 34a, b and rotatable outer ring 30 to base 32. Additionally, the positioning of bearing members 34a, b maintains ratchet members 38a, b in cooperative engagement with ratchet ring 36. In the illustrated embodiment, bearing members 34a, b include a securement member for securing the sutures 22 and 24 during rotation of bearing members 34a, b.

As will be appreciated by those skilled in the art, a variety of types and configurations of bearing members can be utilized without departing from the scope and spirit of the present invention. For example, in one embodiment a circular bearing member is utilized in place of two bearing member segments. In another embodiment, one or more bearing members are integrally coupled to the rotatable outer ring. In yet another embodiment one or more bearing members are integrally coupled to the ratchet members. In another embodiment, the bearing members are positioned above the ratchet ring. In yet another embodiment, a liquid bearing mechanism is utilized. In another embodiment, a roller bearing mechanism is utilized.

In the illustrated embodiment, the path of sutures 20, 22, and 24 relative to sutures storage channel 40 previous to deployment is depicted. Sutures 20, 22 and 24 are looped such that they are positioned inside suture storage channel 40. As a result, when the practitioner secures the anchor device to the patient, the practitioner does not need to manage the positioning of sutures 20, 22, and 24. Suture storage channel 40 in combination with O-ring 28 also maintains the particular desired loop formation of sutures 20, 22, and 24 ensuring proper operation and/or deployment of sutures 20, 22, and 24.

In the illustrated embodiment, first suture channels 52a, b are positioned through base 32 and exiting at extension saddle 44. First suture 20 is configured to be positioned through first suture channels 52a, b such that the ends of first suture 20 extend from extension saddle 44. The extension of the ends of first suture 20 from the extension saddle 44 allows a user to grasp the ends of first suture 20 to actuate first suture 20.

Second suture channels 54a, b and third suture channels 56a, b are positioned through ratchet ring 36 and base 32. Bearing member suture channels 58a, b and 60a, b are positioned through bearing members 34a, b. The second suture 22 and third suture 24 are threaded through suture channels 54a, b; 56a, b; 58a, b; and 60a, b. In more particular, first end 22a of second suture 22 is threaded through second suture channel 54a and bearing member channel 58a, and is secured at the exterior of bearing member 34a. Second end 22b of second suture 22 is threaded through second suture channel 54b, through bearing member channel 60a, and is secured at the exterior of bearing member 34b. First end 24a of third suture 24 is threaded through third suture channel 56a, through bearing member channel 58b and is secured at the exterior of bearing member 34a. Second end 24b of third suture 24 is threaded through third suture channel 56b, through bearing member channel 60b, and is secured at the exterior of bearing member 34b.

Base 32 and ratchet ring 34 are stationary relative to the rotatable outer ring 30. As a result, second suture channel 54a, b and third suture channel 56a, b remain stationary during operation of rotatable ring 14. Bearing members 34a, b rotate in connection with rotatable outer ring 30. As a result, bearing member suture channels 58a, b and 60a, b rotate in connection with rotation of rotatable outer ring 30 and bearing member 34a, b. When bearing members 34a, b rotate in a clockwise direction, the ends of sutures 22 and 24 are drawn around the outside diameter of base 32 beneath ratchet ring 36. As a result, the length of first and second sutures 22 and 24 inside suture storage channel 40 is shortened. As the length of first and second sutures 22 and 24 inside suture storage channel 40 is shortened, the loops of sutures 22 and 24 become smaller such that they can no longer fit in suture storage channel 40. This results in automatic deployment of the loops of sutures 22 and 24 from suture storage channel 40.

Rotatable ratchet members 38a, b engage the teeth of ratchet ring 36 to minimize counterclockwise movement of rotatable ring 14 that would result in loosening of sutures 22 and 24. During rotation of rotatable outer ring 30, bearing members 34a, b and rotatable ratchet members 38a, b are rotated in a clockwise direction about base 32 and in particular ratchet ring 36. Rotatable ratchet members 38a, b engage the teeth of ratchet ring 36 as rotatable ratchet members are advanced 38*a, b* in the clockwise direction. When a user discontinues rotation of rotatable outer ring, rotatable ratchet members 38*a, b* engage the teeth of ratchet ring 36 minimizing movement of rotatable outer ring in a counterclockwise direction that would otherwise loosen second suture 22 and third suture 24.

Rotatable ratchet member 38*a* is positioned between bearing member 34*a* and rotatable outer ring 30. A pivot pin is positioned on the bottom surface of each of the rotatable ratchet members 38*a, b*. The pivot pins are is positioned in rotation bores of the corresponding bearing members 34*a,b* to pivotally couple rotatable ratchet member 34*a* to bearing member 34*a*. Rotatable outer ring 30 contacts the upper surface of rotatable ratchet member 38*a* to maintain contact between the pivot pins and the rotation bores.

The end of rotatable ratchet members 38*a, b* positioned opposite the pivot point provided by the pivot pin of rotatable ratchet member 38*a, b* and the bore of bearing members 34*a,b* include a spring member and a plurality of teeth. The plurality of teeth engage the teeth of ratchet ring 36 to minimize movement of rotatable outer ring 30 and bearing members 34*a,b* in a counterclockwise direction. This spring is provided by the cutaway portion in the head of rotatable ratchet members 38*a,b* and the resilient nature from the material from which the heads of rotatable ratchet members 38*a,b* are constructed. Rotatable ratchet members 38*a, b* will be discussed in more detail with reference to FIGS. 8A and 8B.

In the illustrated embodiment, an O-ring 28 is also illustrated. O-ring 28 is configured to be sandwiched between rotatable outer ring 30 and base 32 to maintain the position of first suture 20, second suture 22, and third suture 24 beneath rotatable ring 14. By maintaining the position of first suture 20, second suture 22, and third suture 24, disruption of the sutures before deployment of the sutures is minimized and reliable and proper operating of anchor device 10 is maintained. As a result, O-ring 28 provides a simple and reliable mechanism for storing first suture 20, second suture 22, and third suture 24 beneath rotatable ring 14 during storage of anchor device 10, during securement of adhesive sheet 12 to the patient, or other aspects of the securement procedure performed before actuation of sutures 20, 22, and 24.

Figure 5A:
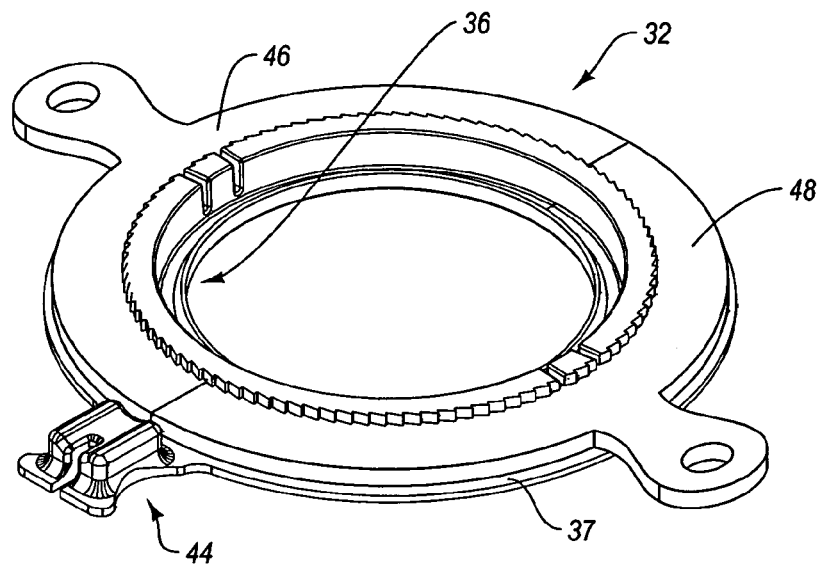
FIGS. 5A and 5B are perspective views of the base of the catheter anchor device illustrating molding of the base utilizing first and second mold members.
Figure 5B:
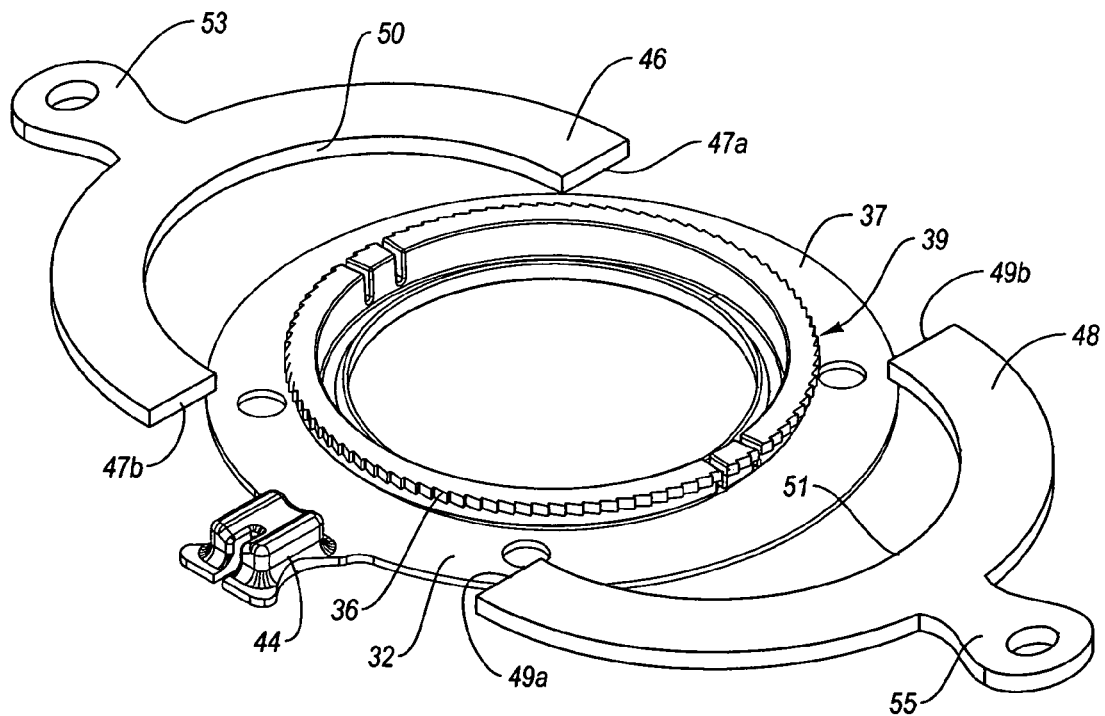

FIGS. 5A and 5B are perspective views of base 32 during molding of base 32. In the illustrated embodiment, base 32 comprises a single molded member formed utilizing first and second mold members 46 and 48. Base 32 comprises a ratchet ring 36 and an extension saddle 44. In the illustrated embodiment, base 32 includes an undercut 39 positioned between ratchet ring 36 and base flange 37. Undercut 39 substantially complicates the molding of base 32. As a result, first mold member 46 and second mold member 48 are utilized to provide the undercut during the molding of base 32. For the sake of clarity, the other mold members utilized to form base 32 have not been illustrated to more clearly depict operation of first mold member 46 and second mold member 48.

In the illustrated embodiment, first mold member 46 comprises mold member interfaces 47*a, b*, an inner circumference 50, and a gripping handle 53. Second mold member 48 comprises mold member interfaces 49*a, b*, an inner circumference 51, and gripping handle 55. During molding, mold member interfaces 47*a, b* of first mold member contact mold member interfaces 49*a, b* of second mold member 48. Inner circumference 50 of first mold member 46 and inner circumference 51 of second mold member 48 form the undercut 39 positioned between ratchet ring 36 and base flange 37. Inner circumference 50 and inner circumference 51 define the inner boundary of undercut 39. The top portion of first mold member 46 and second mold member 48 define the upper lateral surface extending from the innermost horizontal surface of uppercut 39 (not shown) to the edge of ratchet ring 36. The bottom of first mold member 46 and second mold member 48 form the lower horizontal surface which extends from the inner vertical surface of undercut 39 (not shown) and extends outward to be coextensive with base flange 37.

In one embodiment, the surfaces of undercut 39 are slightly flared or tapered to allow for proper releasing of first mold member 46 and second mold member 48 such that when a user grasps gripping handles 53 and gripping handle 55 to pull first mold member 46 and second mold member 48 in a rearward direction, first mold member and second mold member 46, 48, automatically release and can easily be slid from undercut 39. In this manner, base 32 can be molded in single member ensuring continuity of surfaces and reliable and proper operation of the components of base 32 during use of anchor device 10.

As will be appreciated by those skilled in the art, a variety of types and configurations of mechanism can be utilized to mold base 32 in a unitary fashion without departing from the scope and spirit of the present invention. For example, first and second mold members which are configured to be automatically retracted by an automated molding apparatus or other machinery can be utilized. In another embodiment, a single mold member which is hinged, bendable, meltable or otherwise manipulable to remove the mold member from undercut 39 is utilized. In another embodiment, mold members having different form, size, and/or surfaces can be utilized. In another embodiment, more than two mold members are utilized to form the undercut and/or other portions of the base during molding.

Figure 6:
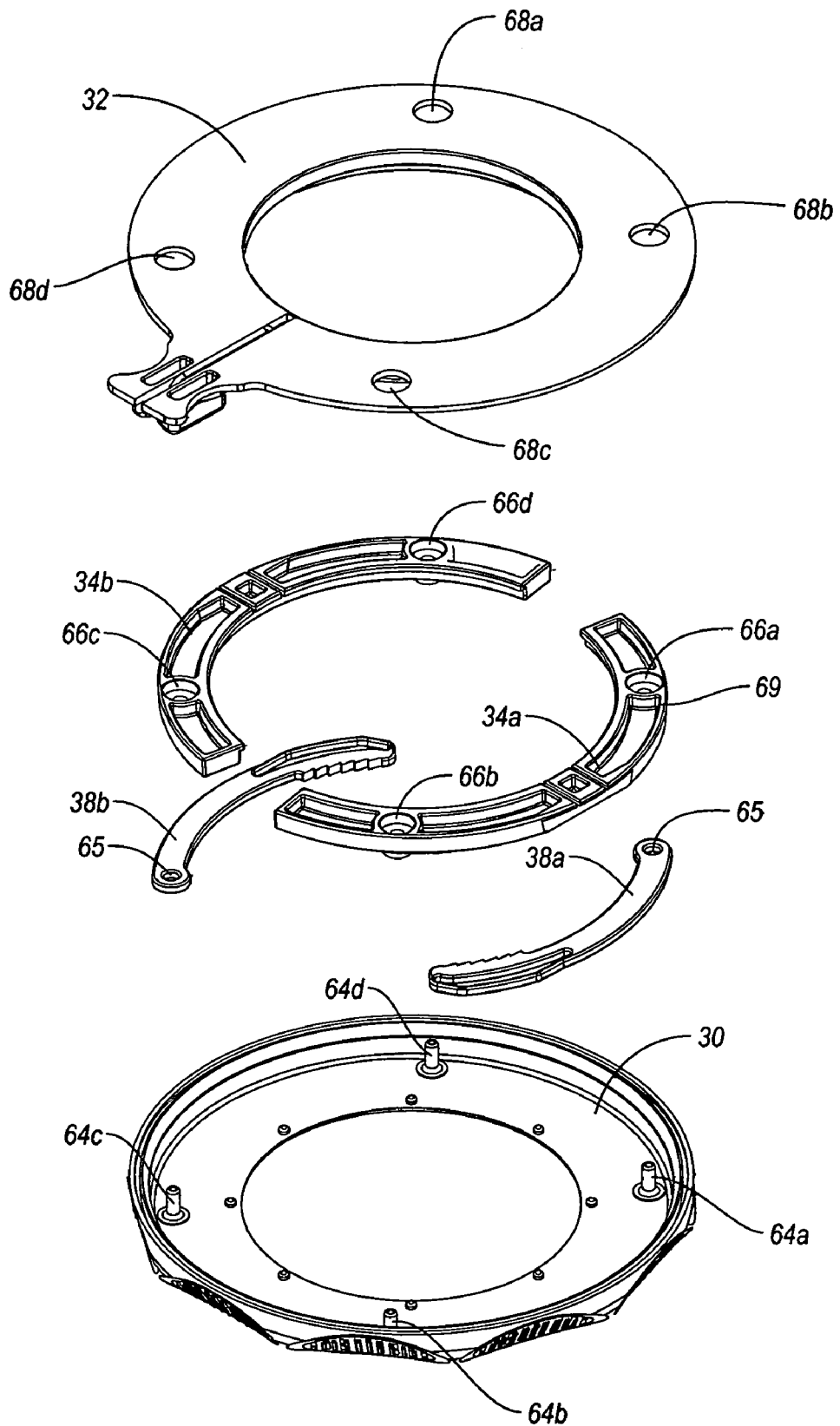
FIG. 6 is an exploded view of the catheter anchor device illustrating components of the catheter anchor device that facilitate assembly of the catheter anchor device utilizing welding of one or more portions of the catheter anchor device.

FIG. 6 is a bottom exploded view illustrating the manner in which the components of anchor device 10 are secured during assembly. In the illustrated embodiment, rotatable outer ring 30, rotatable ratchet member 38*a*, bearing member 34*a*, and base 32 are depicted. Bearing member 34*a* is configured to be sandwiched between rotatable outer ring 30 and base 32. Rotatable ratchet member 38*a* is configured to be positioned between bearing member 34*a* and rotatable outer ring 30. Bearing member 34*a* is configured to be attached directly to rotatable outer ring 30 while being slidable relative to base 32. Pins 64*a-c* are positioned on the underside of rotatable outer ring 30 engage securement bores 66*a-d* of bearing members 34*a, b*. Contact between bearing member 34*a* and base 32 maintains contact between securement bores 66*a-d* and pins 64*a-d*. In the illustrated embodiment, pins 64*a, b* are configured to be welded to securement bores 66*a, b* to integrally couple bearing member 34*a* to rotatable outer ring 30 subsequent to assembly of rotatable outer ring and base 32. Pins 64*c, d* are configured to be welded to securement bores 66*c, d* to integrally couple bearing member 34*b* to rotatable outer ring 30 subsequent to assembly of rotatable outer ring and base 32. A plurality of access bores 68*a-d* are provided in connection with base 32 such that the welding tool can be inserted through access bores 68*a-d* to weld pins 64*a-d* to securement bores 66*a-d* of bearing members 34*a, b*.

Rotatable ratchet member 38*a* is positioned between bearing member 34*a* and rotatable outer ring 30. In the illustrated embodiment, a pivot pin is positioned on the upper surface of bearing member 34*a*. The pivot pin is positioned in rotation bore 65 to pivotally couple rotatable ratchet member 34*a* to bearing member 34*a*. Rotatable outer ring 30 contacts the upper surface of rotatable ratchet member 38*a* to maintain contact between the pivot pins and rotation bore 65. Additionally, the outer horizontal portion of the rotatable outer ring which extends downward adjacent rotatable ratchet member 38a contains lateral movement of the free end of rotatable ratchet member 38a to ensure proper operation and contact between the teeth of rotatable ratchet member 38a and the teeth of ratchet ring 36 (illustrated in FIGS. 5A and 5B).

As will be appreciated by those skilled in the art, a variety of types and configurations of mechanisms for securing the components of the rotatable ring can be utilized without departing from the scope and spirit of the present invention. For example, in one embodiment, the bearing member is configured to be welded to the rotatable outer ring previous to assembly with the base. In another embodiment, a snap fitting is provided between the bearing member and the rotatable outer ring. In another embodiment, a continuous bearing member is integrated with the base 32 while the rotatable ratchet member is secured independently to the rotatable outer ring. In yet another embodiment, a surface is provided on the bearing member to maintain proper operation of the rotatable ratchet member.

Figure 7A:
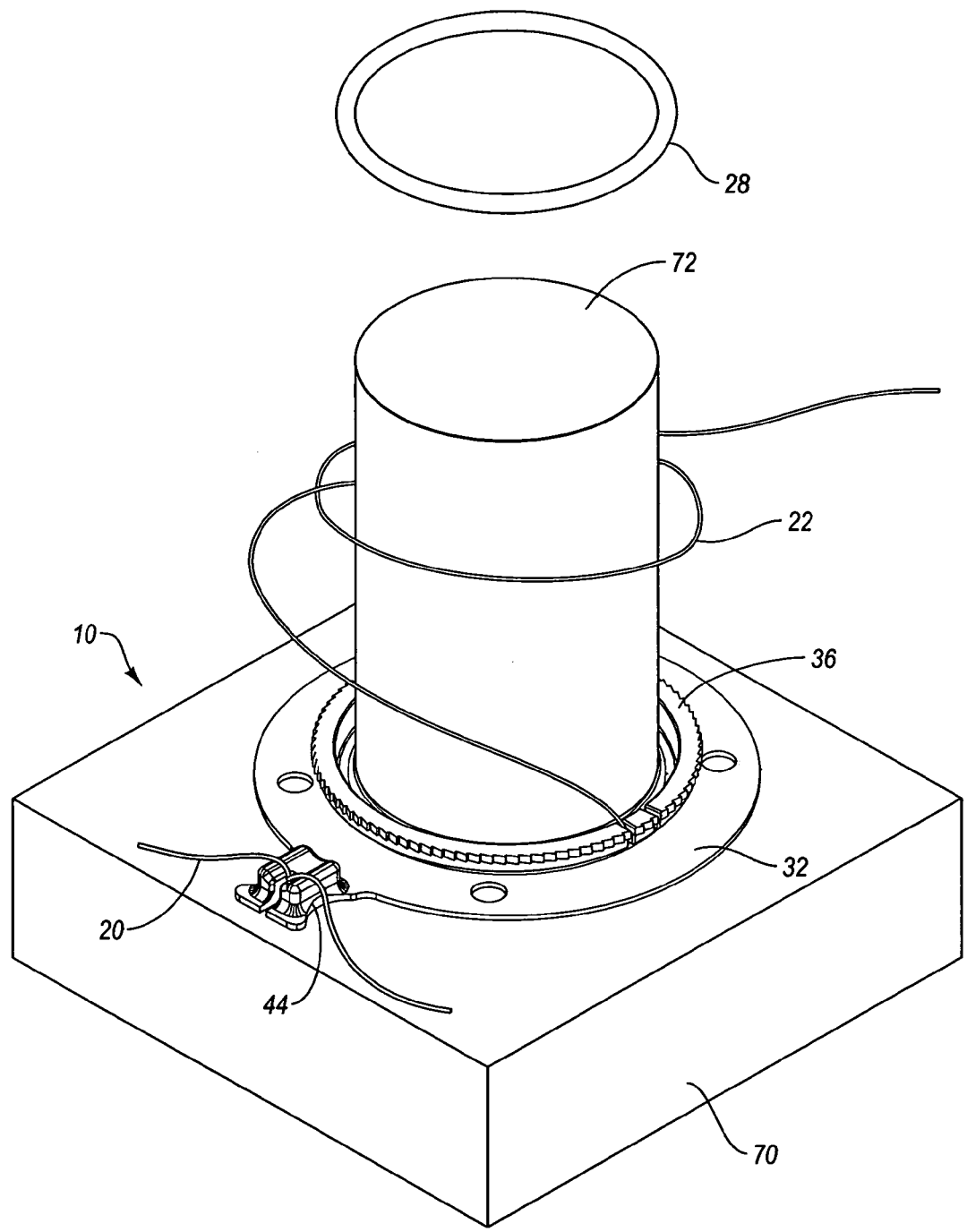
FIGS. 7A and 7B are perspective views of the base of the catheter anchor device illustrating loading of the sutures during assembly of the catheter anchor device.
Figure 7B:
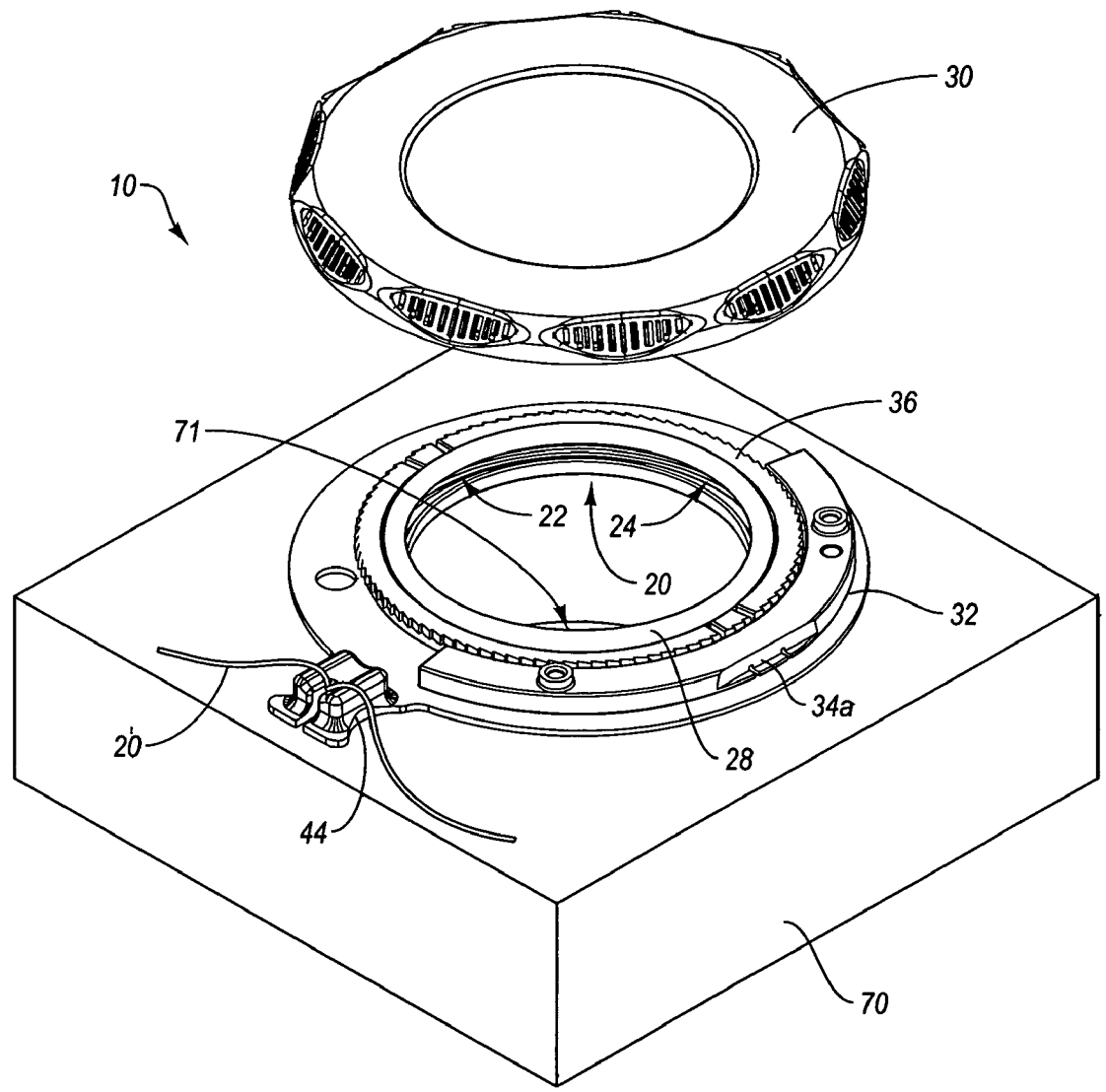

FIGS. 7A and 7B illustrate loading of the sutures utilized with anchor device, according to one embodiment of the present invention. In the illustrated embodiment, base 32 of anchor device 10 is mounted on a loading block 70. Center aperture 16 of anchor device 10 is positioned over the center bore 71 of loading block 70. A suture loading cylinder 72 is positioned through center bore 71 and center aperture 16 such that the wall of the suture loading cylinder 72 is positioned adjacent the inner portion of ratchet ring 36. Suture loading cylinder 72 is utilized to provide a quick and effective mechanism for forming the loop configurations of first suture 20, second suture 22, and third suture 24 (not shown) and for loading the sutures in base 32.

In the illustrated embodiment, the loops of second suture 22 are being formed around suture loading cylinder 72. First suture 20 has previously been loaded into base 32 utilizing suture loading cylinder 72. One end of second suture 22 has been threaded through and secured relative to base 32. The loop has been substantially formed by wrapping the length of second suture 22 about suture loading cylinder 72 in a manner so as to produce the desired configuration of the loop portion of second suture 22. The second end of second suture 22 is positioned freely, as it has not yet been secured relative to base 32. Once the loop has been formed in second suture 22, the loop portion of second suture 22 will be drawn tightly around suture loading cylinder 72 by pulling on the second end of second suture 22. The second end of second suture 22 will then be threaded relative to base and secured to one of the bearing members 34a, b (bearing member 34b not shown).

As the loop portion of second suture 22 is drawn tight and the second end of second suture 22 is secured relative to one of bearing members 34a, b and base 32, the loop portion of second suture 22 is automatically drawn down such that it is loaded within ratchet ring 36 in the desired position for deployment. As will be appreciated by those skilled in the art, similar steps, acts, and processes are utilized to load first suture 20 and third suture 24. The discussion of the formation of loops of second suture 22 and the loading of second suture 22 in base 32 is discussed for illustrative purposes and should in no way be considered to be limiting in nature.

Once first suture 20, second suture 22, and third suture 24 have been properly loaded in base 32, O-ring 28 is positioned over the top of suture loading cylinder 72. O-ring 28 is lowered along the length of suture loading cylinder 72 until it is positioned along the inner circumference of ratchet ring 36 effectively maintaining the position of first suture 20, second suture 22, and third suture 24 in their desired position within base 32. Once O-ring 28 has been properly positioned within base 32, suture loading cylinder 72 is withdrawn from center aperture 16 and rotatable outer ring 30 is lowered into engagement with base 32 as discussed with respect to FIG. 6. The proper steps can then be taken to couple rotatable outer ring 30 to bearing member 34a, b as discussed with respect to FIG. 6.

As will be appreciated by those skilled in the art, a variety of types and configurations of mechanism for loading the sutures in the base can be utilized without departing from the scope and the spirit of the present invention. For example, in one-embodiment, a loading block and suture loading cylinder are utilized to manually load the sutures in the anchor device. In another embodiment, the loading block and suture loading cylinder are utilized with automated processes to load the suture into the base or other component of the anchor device.

Figure 8A:
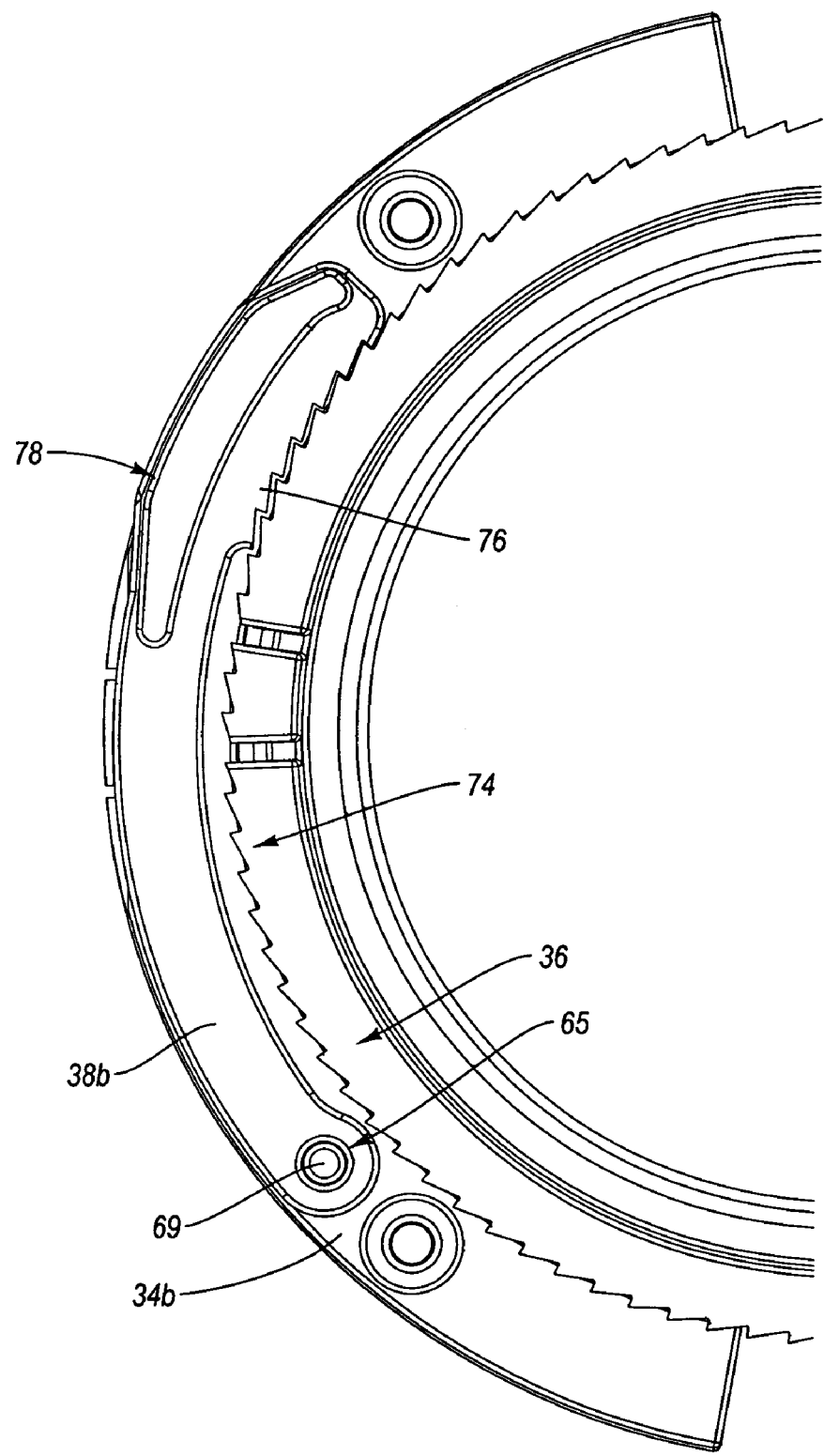
FIGS. 8A and 8B are component views illustrating the ratchet mechanism including operation of a rotatable ratchet member relative to the ratchet ring.
Figure 8B:
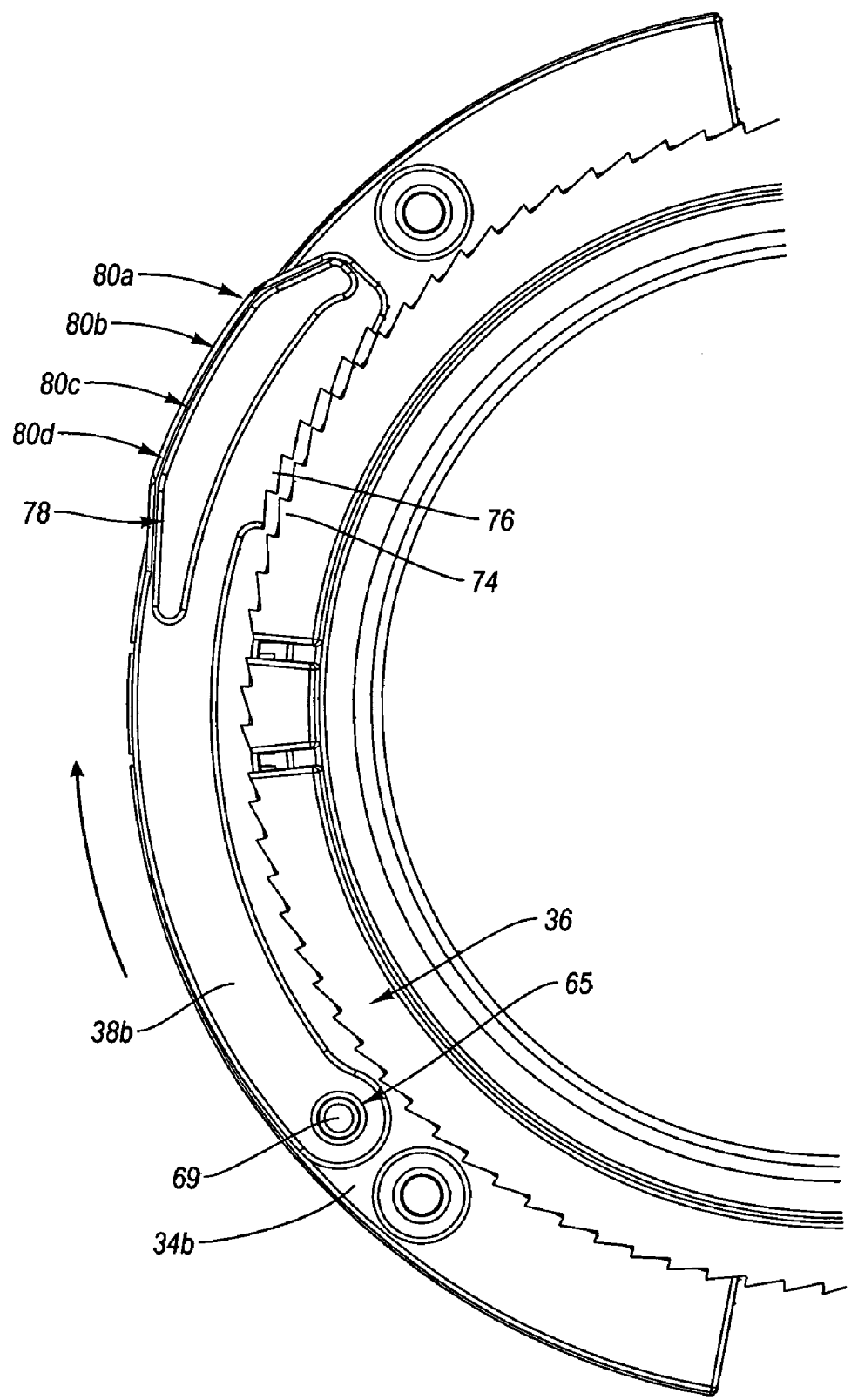

FIGS. 8A and 8B illustrate rotatable ratchet member 38b in operation with respect to ratchet ring 36. While rotatable ratchet member 38b is shown for illustrative purposes, it will be understood by those skilled in the art that operation of rotatable ratchet member 38b also is exemplary of rotatable ratchet member 38a (see FIG. 4.) In the illustrated embodiment, rotatable ratchet member 38b is rotatably coupled to bearing member 34b utilizing pivot pin 69 and rotation bore 65 of rotatable ratchet member 34b. Rotatable ratchet member 38ab engages the teeth of ratchet ring 36 to minimize counterclockwise movement of rotatable ring 14 that would result in loosening of sutures 22 and 24. Rotatable ratchet member 38b is secured to bearing member 34b by pivot pin 69 located between the upper surface of bearing member 34b and the bottom surface of rotatable outer ring 30 (see FIG. 4). Pivot pin 69 is positioned in the rotation bore 65 of rotatable ratchet member 38b such that rotatable ratchet member 38b can pivot about pivot pin 69.

The rotatable ratchet member 38b is held in place relative to bearing member 34b by being sandwiched between bearing member 34b and rotatable outer ring 30 (see FIG. 4). Thus, during rotation of rotatable outer ring 30 (see FIG. 4), bearing member 34b and rotatable ratchet member 38b are rotated in a clockwise direction about ratchet ring 36. Rotatable ratchet member 38b engages the teeth of ratchet ring 36 as rotatable ratchet member is advanced 38b in the clockwise direction. When a user discontinues rotation of the rotatable outer ring, rotatable ratchet member 38b engages the teeth of ratchet ring 36 minimizing movement of rotatable outer ring 30 in a counterclockwise direction that would otherwise loosen the sutures.

The end of rotatable ratchet member 38b positioned opposite the rotation bore 65 and pivot pin includes a ratchet member engagement spring 78 and rotatable ratchet member teeth 76. Rotatable ratchet member teeth 76 engage the ratchet ring teeth 74 to minimize movement of the rotatable outer ring and bearing member 34b in counterclockwise direction. Ratchet member engagement spring 78 is provided by the cutaway portion in the head of rotatable ratchet member 38b. The nature of the material from which the head of rotatable ratchet member 38b is constructed provides sufficient resilience to undergo deformation while maintaining contact between rotatable ratchet member teeth 76 and ratchet ring teeth 74.

As the rotatable ratchet member teeth 76 slide over ratchet ring teeth 74, ratchet member engagement spring 78 flexes slightly to maintain contact between rotatable ratchet member teeth 76 and ratchet ring teeth 74. This is caused by the ramp-like configuration of rotatable ratchet member teeth 76 and ratchet ring teeth 74. When the rotatable ratchet member teeth 76 pass over the outer most ridge of ratchet ring teeth 74 such that they engage new teeth, ratchet member engagement spring 78 forces the rotatable ratchet member teeth 76 toward the center of the anchor device 10, thus maintaining, engagement with ratchet ring teeth 74.

As will be appreciated by those skilled in the art, a variety of types and configurations of rotatable ratchet members can be utilized without departing from the scope and spirit of the present invention. For example, in one embodiment, the rotatable ratchet members prevent rotation of a rotatable ring in a clockwise direction. In another embodiment, the rotatable ratchet members prevent backward movement of a nonrotational actuation member. In another embodiment, a secondary spring separate from the body of the rotatable ratchet member provides the spring movement of all or part of the rotatable ratchet member.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter anchor device for use with a catheter which is inserted into a patient at a catheter insertion site for minimizing movement of the catheter that could result in pressure, discomfort, or tearing at the catheter insertion site, the catheter anchor device configured to automatically deploy one or more sutures to quickly and efficiently secure the catheter, the anchor device comprising:

an adhesive layer configured to be secured to the skin of the patient proximate the catheter insertion site that allows access to the catheter insertion site and permits a practitioner to view and clean the catheter insertion site;

a stationary base secured to the adhesive layer;

a rotatable ring circumscribing the stationary base such that the rotatable outer ring can be rotated by the user relative to the stationary base; and one or more sutures having a stowage position, wherein when the sutures are in the stowage position the sutures are positioned between the stationary base and the rotatable ring, wherein the one or more sutures are operably coupled to the rotatable ring such that actuation of the rotatable ring automatically deploys the one or more sutures from the stowage position to secure the catheter relative to the rotatable ring; and an O-ring that secures the sutures between the stationary base and the rotatable ring before deployment of the sutures while allowing deployment of the sutures upon actuation of the rotatable ring.

2. The catheter anchor device of claim 1, wherein the O-ring is positioned between the stationary base and the rotatable outer ring.

3. The catheter anchor device of claim 1, wherein the sutures are stored in a suture storage channel previous to actuation of the sutures.

4. The catheter anchor device of claim 3, wherein the suture storage channel is positioned in the stationary base.

5. The catheter anchor device of claim 3, wherein the suture storage channel is positioned in the rotatable ring.

6. The catheter anchor device of claim 3, wherein the suture storage channel comprises a flexible flange.

7. The catheter anchor device of claim 6, wherein the O-ring secures the sutures in the suture storage channel in cooperation with the flexible flange.

8. The catheter anchor device of claim 1, wherein the O-ring is non-circular.

9. The catheter anchor device of claim 1, further comprising a supplemental O-ring which cooperates with the O-ring to maintain the position of the sutures before deployment of the sutures.

* * * * *